US008695428B2

(12) United States Patent
Lee et al.

(10) Patent No.: US 8,695,428 B2
(45) Date of Patent: Apr. 15, 2014

(54) SINGLE INPUT MULTI-OUTPUT SURFACE ACOUSTIC WAVE DEVICE

(75) Inventors: Yeol ho Lee, Seoul (KR); Soo Suk Lee, Suwon-si (KR); Kee Keun Lee, Yongin-si (KR)

(73) Assignees: Samsung Electronics Co., Ltd., Suwon-Si (KR); Ajou University Industry-Academic Cooperation Foundation, Suwon-Si (KR)

( * ) Notice: Subject to any disclaimer, the term of this patent is extended or adjusted under 35 U.S.C. 154(b) by 245 days.

(21) Appl. No.: 13/172,431

(22) Filed: Jun. 29, 2011

(65) Prior Publication Data

US 2012/0105174 A1 May 3, 2012

(30) Foreign Application Priority Data

Oct. 29, 2010 (KR) .................. 10-2010-0106534

(51) Int. Cl.
*G01N 29/024* (2006.01)
*G01N 29/036* (2006.01)
*H01L 41/04* (2006.01)
*H01L 41/08* (2006.01)

(52) U.S. Cl.
USPC ............. 73/579; 73/597; 73/24.01; 73/24.06; 310/313 R; 310/313 B; 310/313 D

(58) Field of Classification Search
USPC .......... 73/579, 597, 657, 29.01–29.02, 24.01, 73/24.06, 31.05–31.06; 310/313 R, 313 A, 310/313 B, 313 D; 333/193–195
See application file for complete search history.

(56) References Cited

U.S. PATENT DOCUMENTS

| 3,479,572 | A  | * | 11/1969 | Pokorny ......................... 257/254 |
| 3,898,592 | A  | * | 8/1975  | Solie ............................... 333/195 |
| 4,926,146 | A  | * | 5/1990  | Yen et al. ....................... 333/195 |
| 5,256,927 | A  | * | 10/1993 | Kato et al. ................. 310/313 B |
| 6,078,608 | A  | * | 6/2000  | Ohtsuka et al. ............... 375/130 |
| 6,534,896 | B2 | * | 3/2003  | Jian et al. .................. 310/313 B |
| 6,541,893 | B2 | * | 4/2003  | Zhu et al. .................. 310/313 B |
| 7,047,792 | B1 | * | 5/2006  | Bhethanabotla et al. .... 73/24.01 |
| 7,053,523 | B1 | * | 5/2006  | Ballato et al. ............. 310/313 B |
| 7,134,319 | B2 | * | 11/2006 | Liu ................................. 73/31.06 |
| 7,202,589 | B2 | * | 4/2007  | Kalinin et al. ............ 310/313 D |
| 7,762,124 | B2 |   | 7/2010  | Okaguchi et al. |
| 7,855,564 | B2 | * | 12/2010 | Sabah et al. .................. 324/600 |
| 7,888,842 | B2 | * | 2/2011  | Pereira da Cunha et al. . 310/324 |
| 7,936,106 | B2 | * | 5/2011  | Lee et al. .................. 310/313 R |
| 8,143,681 | B2 | * | 3/2012  | Zaghloul et al. ............. 257/416 |
| 2008/0084135 | A1 | * | 4/2008 | Ramsesh et al. .......... 310/313 R |
| 2009/0124513 | A1 |   | 5/2009 | Berg et al. |
| 2009/0280593 | A1 | * | 11/2009 | Serban et al. ................... 438/49 |
| 2010/0058834 | A1 | * | 3/2010 | Cobianu et al. .............. 73/24.01 |
| 2011/0068656 | A1 | * | 3/2011 | Lee et al. .................. 310/313 C |
| 2011/0111516 | A1 | * | 5/2011 | Lee et al. ...................... 436/149 |
| 2011/0236877 | A1 | * | 9/2011 | Yao et al. ......................... 435/4 |

FOREIGN PATENT DOCUMENTS

KR    10-2006-0052296    6/2008
WO    2006/114829        11/2006

* cited by examiner

*Primary Examiner* — Helen Kwok
(74) *Attorney, Agent, or Firm* — Leydig, Voit & Mayer, Ltd.

(57) ABSTRACT

A single-input multi-output surface acoustic wave ("SAW") device contains two or more output inter-digital transducers ("IDTs") arranged in a longitudinal direction of a single input IDT. The detection sensitivity and reliability of the SAW device may be improved by eliminating the deviation and signal interference between multiple input IDTs.

17 Claims, 14 Drawing Sheets

SINGLE INPUT MULTI-OUTPUT SURFACE ACOUSTIC WAVE DEVICE

CROSS-REFERENCE TO RELATED APPLICATION

This application claims priority to Korean Patent Application No. 10-2010-0106534, filed on Oct. 29, 2010, and all the benefits accruing therefrom under 35 U.S.C. §119, the content of which in its entirety is herein incorporated by reference.

BACKGROUND OF THE INVENTION

1. Field of the Invention

This disclosure relates to a single-input multi-output surface acoustic wave device.

2. Description of the Related Art

A surface acoustic wave ("SAW") is not an electromagnetic wave, but rather is a pressure wave that is generated by the displacement of particles. This displacement of particles can be brought about by external factors, such as, for example, thermal, mechanical, and/or electrical forces. As a result, a majority of the vibrational energy in the SAW is concentrated on the surface of a medium. A SAW sensor is a device that senses the presence or properties of a target material using surface acoustic waves. Generally, the SAW sensor is disposed on a substrate that includes a piezoelectric material, and the SAW sensor includes a receptor that specifically binds to a target material. When a solution containing the target material flows to the SAW sensor, its wavelength is changed by a physical, chemical and electrical interactions between the target material and the receptor. Accordingly, the content of the target material can be detected and monitored by the change in the signal change caused by the change in the wavelength.

The SAW sensor is sensitive to changes in pressure of a fluid, and viscosity or density of a medium, as well as mass on the surface. Thus, it is very important to minimize any noise that could cause a change in the signal other than that caused by the sample that is to be detected.

In a typical SAW sensor, an oscillation technique of applying an output signal emitted from an output inter-digital transducer ("IDT") of the SAW sensor to an input IDT of the SAW sensor is used to generate a surface acoustic wave in an electrode of the SAW sensor. Further, a technique of generating a certain frequency outside the SAW sensor includes applying the frequency to an input IDT, and plotting an emitted output signal output of the SAW sensor.

SUMMARY OF THE INVENTION

Exemplary embodiments provide a surface acoustic wave ("SAW") device. The SAW device may not experience or have experienced substantially reduced amount of the error and deviation of signal which generally occurs in a multi-input and multi-output structure having a plurality of input inter-digital transducers ("IDTs") and a plurality of corresponding output IDTs being arranged in pairs.

According to an exemplary embodiment, a SAW device includes: a piezoelectric substrate; a single input IDT disposed on the piezoelectric substrate, the input IDT converting an electrical signal into a SAW signal; a plurality of output IDTs disposed on the piezoelectric substrate, the output IDTs converting the SAW signal into the electrical signal; and a delay line placed between the input IDT and the output IDTs. Here, at least two of the output IDTs are arranged in a longitudinal direction of the input IDT.

In one embodiment, the input IDT may include fingers, and each finger has a length such that an insertion loss ("IL") of the input IDT represented by Formula (1) and (2) below is less than −30 dB.

$$IL = -20 \log |Y| \quad (1)$$

$$Y = Y_0(W/\lambda) \quad (2)$$

where Y is the total input admittance, $Y_0$ is a characteristics admittance, $\lambda$ is a wave length and W is a finger length.

The length of the finger of the input IDT (i.e. $W=W_{in}$) may have a maximum value of $300\lambda$, where $\lambda$ is the wavelength of the surface acoustic wave.

In one embodiment, the number (m) of the output IDTs may be represented by Formula (3) below:

$$m = \frac{2W_{in}}{W_{out}} \quad (3)$$

where $W_{in}$ is the length of each finger of the input IDT, and $W_{out}$ is the length of each finger of each output IDT.

In another embodiment, when the length of each finger of each output IDT is $50\lambda$, the number of output IDTs with the single input IDT may be in a range from 2 to 12.

In the embodiment, the SAW may include a Love wave. The piezoelectric substrate may include a dielectric layer or a polymer layer.

In the embodiment, the input IDT may be connected with an external resonator.

In the exemplary embodiment, the SAW device may further include additional output IDTs where the input inter-digital transducer is located between the additional output IDTs and the output IDTs. In the embodiment, the SAW device may be a SAW sensor. In the SAW sensor, a receptor reacts with a target material. The receptor interacted with or bonded to the target material is immobilized on the delay line. The SAW sensor can then detect the difference between the receptor bonded to the target material and a reference sample. This difference results in a detection of the target material. This SAW sensor may be used to detect a change in signal output from the output IDTs to analyze two or more of mass, pressure, density and viscosity of the target material.

According to another exemplary embodiment, a SAW device includes: a substrate; a transmitter disposed on the substrate, the transmitter generating a surface acoustic wave ("SAW"); at least two receivers disposed on the substrate, the receivers receiving the SAW and converting the received SAW into an electrical signal; and a receptor disposed between the transmitter and the receivers, the receptor reacting to or interacting with a target material.

In the embodiment, the transmitter and the receivers may be disposed on a surface of the same substrate.

In one embodiment, the SAW may include a Love wave.

In another embodiment, the at least two receivers are arranged in parallel to a longitudinal direction of the transmitter.

In yet another embodiment, the at least two receivers are disposed opposite each other and are equally spaced from the transmitter. They are disposed opposite from each other with the transmitter being disposed in the center of the two receivers.

The SAW devices described above make it possible to sense a plurality of target materials within a single SAW device. The design makes it possible to reduce interference and noise that is generally associated with electrical signals from electrical components in a device that are disposed proximately to one another. In another embodiment, it is possible to reduce the size of the SAW device when compared with other comparative commercially available devices by integrating the sensor in the manner described. It is also possible to remarkably reduce amount of a testing solution for the SAW device where the testing solution includes the materials to be detected. This is desired when the sample has to be extracted from a patient. In addition, the SAW device can be applied to the oscillation method, and thus provides high sensitivity, excellent economical efficiency, and excellent industrial effective value.

Disclosed herein too is a method of manufacturing a surface acoustic wave device comprising: disposing a single input inter-digital transducer on a piezoelectric substrate, the input inter-digital transducer converting a first electrical signal into a surface acoustic wave signal; disposing a plurality of output inter-digital transducers on the piezoelectric substrate, the output inter-digital transducers converting the surface acoustic wave signal into a second electrical signal; and disposing a delay line between the input inter-digital transducer and the output inter-digital transducers, wherein the plurality of the output inter-digital transducers are arranged in a longitudinal direction of the input inter-digital transducer.

The method may further comprising disposing a plurality of surface wave acoustic devices on a surface that rotates, the surface rotating about a vertical axis or a horizontal axis.

Disclosed herein to is a method of using a surface acoustic wave device comprising reacting a target material with a receptor; disposing the target material reacted with the receptor on a surface acoustic wave device; wherein the surface acoustic wave device comprises a piezoelectric substrate; a single input inter-digital transducer disposed on the piezoelectric substrate; a plurality of output inter-digital transducers disposed on the piezoelectric substrate; and a delay line between the input inter-digital transducer and the output inter-digital transducers, wherein the plurality of the output inter-digital transducers are arranged in a longitudinal direction of the input inter-digital transducer; wherein the target material reacted with the receptor are disposed on the delay line; converting a first electrical signal into a surface acoustic wave signal at the input inter-digital transducer; and convert the surface acoustic wave signal into a second electrical signal at the output inter-digital transducer.

BRIEF DESCRIPTION OF THE DRAWINGS

The above and other aspects, advantages and features of this invention will become more apparent by describing in further detail exemplary embodiments thereof with reference to the accompanying drawings, in which.

DETAILED DESCRIPTION OF THE INVENTION

Figure 1:
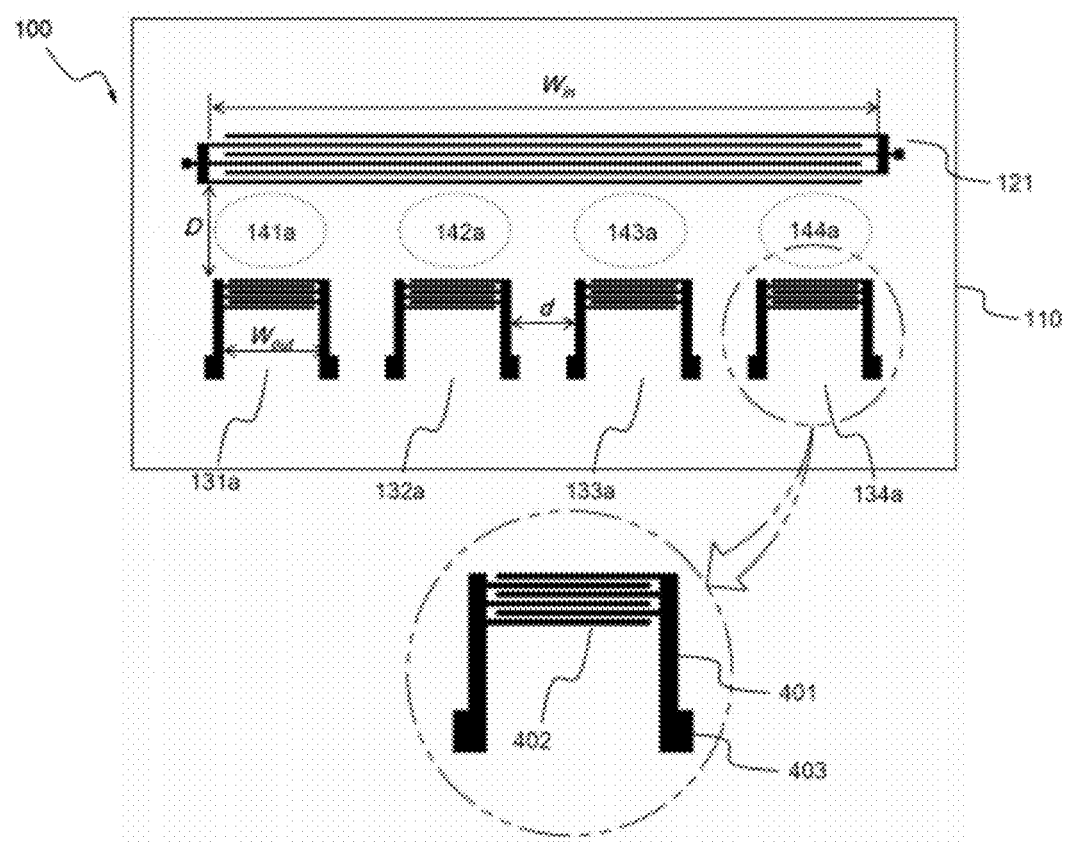
FIG. 1 schematically illustrates an exemplary embodiment of a SAW device.

This invention now will be described more fully hereinafter with reference to the accompanying drawings, in which various embodiments are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated regions, integers, steps, operations, elements, and/or components, but do not preclude the presence or addition of one or more other regions, integers, steps, operations, elements, components, and/or groups thereof.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation depicted in the figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the disclosure, and will not be interpreted in an idealized or overly formal sense unless expressly so defined herein.

Embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein, but are to include deviations in shapes that result, for example, from manufacturing. For example, a region illustrated or described as flat may, typically, have rough and/or nonlinear portions. Moreover, sharp angles that are illustrated may be rounded. Thus, the regions illustrated in the figures are schematic in nature and their shapes are not intended to illustrate the precise shape of a region and are not intended to limit the scope of the claims.

For convenience, a "surface acoustic wave" used herein may be abbreviated to "SAW". The term "surface acoustic wave device" or "SAW device" may be understood to include all of a SAW filter, a SAW sensor, a SAW resonator, or a combination comprising at least one of the foregoing SAW devices. Further, the same reference numerals used throughout the different drawings to designate the same elements may be omitted.

FIG. 1 schematically illustrates an exemplary embodiment of a SAW device.

Referring to FIG. 1, the SAW device 100 includes a substrate 110, an input inter-digital transducer ("IDT") 121 disposed on the substrate 110, output IDTs 131a, 132a, 133a and 134a disposed corresponding to the input IDT 121, and delay lines 141a, 142a, 143a and 144a interposed between the input IDT 121 and the output IDTs 131a, 132a, 133a and 134a. An interdigital transducer (IDT), or interdigitated transducer, is a device which consists of two interlocking comb-shaped metallic coatings that is disposed on the substrate 110.

The substrate 110 includes a piezoelectric material. The piezoelectric material has an electrical characteristic that is changed when a mechanical signal is applied (i.e., the piezoelectric effect). Conversely, a mechanical signal is generated when an electrical signal is applied (i.e., the reverse piezoelectric effect).

As noted above, the substrate may include piezoelectric materials which are dielectrics and comprise mainly metal oxides. The metal oxides may include, for example, but is not limited to, lithium niobate ("LiNbO$_3$"), lithium tantalate ("LiTaO$_3$"), lithium tetraborate ("Li$_2$B$_4$O$_7$"), barium titanate ("BaTiO$_3$"), lead zirconate ("PbZrO$_3$"), lead titanate ("PbTiO$_3$"), lead zirconate titanate ("PZT"), zinc oxide ("ZnO"), gallium arsenide ("GaAs"), quartz and niobate, berlinite, topaz, tourmaline group materials, potassium niobate, lithium niobate, sodium tungstate, Ba$_2$NaNb$_5$O$_5$, Pb$_2$KNb$_5$O$_{15}$, or the like, or a combination comprising at least one of the foregoing piezoelectric materials.

In another embodiment, the substrate may comprise piezoelectric polymers or copolymers or blends comprising at least one piezoelectric polymer. A suitable example of a piezoelectric polymer is polyvinylidene fluoride.

Blends and copolymers of the polyvinylidene fluoride can also be used in the substrate. The copolymers can include block copolymers, alternating block copolymers, random copolymers, random block copolymers, graft copolymers, star block copolymers, or the like, or a combination comprising at least one of the foregoing thermoplastic polymers.

Examples of suitable polymers that can be copolymerized with polyvinylidene fluoride are polytrifluoroethylene, polytetrafluoroethylene, polyacrylamide, polyhexafluoropropylene, polyacrylic acid, poly-(N-isopropylacrylamide), polyacetals, polyolefins, polyacrylics, polycarbonates, polystyrenes, polyesters, polyamides, polyamideimides, polyarylates, polyarylsulfones, polyethersulfones, polyphenylene sulfides, polyvinyl chlorides, polysulfones, polyimides, polyetherimides, polytetrafluoroethylenes, polyetherketones, polyether etherketones, polyether ketone ketones, polybenzoxazoles, polyphthalides, polyacetals, polyanhydrides, polyvinyl ethers, polyvinyl thioethers, polyvinyl alcohols, polyvinyl ketones, polyvinyl halides, polyvinyl nitriles, polyvinyl esters, polysulfonates, polysulfides, polythioesters, polysulfones, polysulfonamides, polyureas, polyphosphazenes, polysilazanes, or the like, or a combination comprising at least one of the foregoing thermoplastic polymers. This list of thermoplastic polymers includes polymers that are electrically insulating. These thermoplastic polymers may be rendered electrically conductive by the addition of intrinsically conductive polymers or electrically conducting fillers to the respective polymers.

In one embodiment, the piezoelectric material may included a composite that comprises a polymer blended with other piezoelectric polymers. The piezoelectric polymer may comprise other fillers that display piezoelectric properties to form a piezoelectric composition. Examples of these piezoelectric fillers are lithium niobate ("LiNbO$_3$"), lithium tantalate ("LiTaO$_3$"), lithium tetraborate ("Li$_2$B$_4$O$_7$"), barium titanate ("BaTiO$_3$"), lead zirconate ("PbZrO$_3$"), lead titanate ("PbTiO$_3$"), lead zirconate titanate ("PZT"), zinc oxide ("ZnO"), gallium arsenide ("GaAs"), quartz and niobate, berlinite, topaz, tourmaline group materials, potassium niobate, lithium niobate, sodium tungstate, Ba$_2$NaNb$_5$O$_5$, Pb$_2$KNb$_5$O$_{15}$, or the like, or a combination comprising at least one of the foregoing piezoelectric materials.

When piezoelectric fillers are added to the piezoelectric polymer to form the piezoelectric material, they can be added in amounts of up to about 50 weight percent (wt %), or in amounts of about 0.001 to about 5 wt %, or in amounts of about 0.01 to about 1 wt %, based on the total weight of the piezoelectric composition.

The delay lines 141a, 142a, 143a and 144a are reaction areas at which target materials may be bound to a receptor and immobilized for sensing the target materials. Depending on the number of the delay lines, the number of target materials that can be sensed by the SAW device 100 may be determined. In the exemplary embodiment, the four delay lines 141a, 142a, 143a and 144a are disposed, thus three or four target materials, which are different from each other, may be sensed at the same time or sequentially.

The number of delay lines can be from about 2 to about 12, or about 4 to about 10, or about 6 to about 8. In one embodiment, the number of delay lines can be from about 4 to about 6.

These delay lines or reaction areas/sections 141a, 142a, 143a and 144a may include receptors specifically reacting (or interacting) with the target materials. The receptor may include a gas adsorbent, an enzyme, a microbe, an antibody, a deoxyribonucleic acid (DNA), a protein, a glycoprotein, a cytokine, a mixture of proteins, or a combination comprising at least one of the foregoing proteins. The reaction section may have a shape of a membrane or a cell that immobilizes the receptor.

The input IDT 121 and the output IDTs 131a, 132a, 133a and 134a are disposed opposite one another. The input IDT 121 generates a surface acoustic wave by an applied first electrical signal. Therefore, the input IDT 121 may be referred to as a "transmitter." The surface acoustic wave generated may be transmitted along the surface of the substrate 110 to the output IDTs 131a, 132a, 133a and 134a through expansion and compression at a selected frequency, and then converted into a second electrical signal by the reverse piezoelectric effect. These output IDTs 131a, 132a, 133a and 134a may be referred to as "receivers." The transmitter and the receivers may be disposed on a surface of the same substrate 110 (as shown in FIG. 1).

Referring to an enlarged view showing one of the output IDTs in the FIG. 1, each IDT electrode includes two bar-shaped electrodes 401, and a plurality of fingers 402 that extend horizontally from each bar-shaped electrode. The fingers 402 extending from one of the bar-shaped electrodes 401 may alternate with those extending from the other bar-shaped electrode. Connection electrodes 403 may be electrically connected to the bar-shaped electrodes 401.

The IDT electrode may include, but is not limited to, a thin-film metal, an electrically conducting ceramic or an electrically conducting plastic. Examples of thin-film metals are an aluminum alloy, a copper alloy, or gold, or the like, or a combination comprising at least one of the foregoing metals. Examples of thin-film ceramics are indium oxide, indium tin oxide, fluorine doped tin oxide (FTO), doped zinc oxide, or the like, or a combination comprising at least one of the foregoing metal oxides.

Examples of thin-film electrically conducting polymers include intrinsically conducting polymers or electrically insulating polymers that are made electrically conducting by the addition of electrically conducting fillers. Examples of intrinsically conducting polymers are polyaniline, polypyrrole, polyacetylene, polythiophene, or the like, or a combination comprising at least one of the foregoing intrinsically conducting polymers.

As noted above, the thin-film electrically conducting polymer may be an electrically insulating polymer that is compounded with an electrically conducting filler. A list of electrically insulating polymers is provided above. Electrically conducting fillers are metal particles (e.g., metal whiskers, metal fibers, and the like), carbon nanotubes, carbon black, graphite, indium tin oxide particles and whiskers, or the like, or a combination comprising at least one of the foregoing electrically conducting fillers.

In order to prevent corrosion of the IDT electrode when exposed to atmosphere or moisture, a protective layer such as an anti-oxidation layer may be formed on the surface of the IDT electrode. For example, the IDT electrode may include aluminum or an aluminum alloy, and an aluminum oxide thin film formed on the surface thereof as the anti-oxidation layer. The aluminum alloy may include Al as a main component, and at least one of Ti, Si, Cr, W, Fe, Ni, Co, Pb, Nb, Ta, Zn, and V. The aluminum oxide thin film may be an artificially or natively formed aluminum oxide.

An insulation layer may be formed to insulate the IDT electrode. The insulation layer may be used as a waveguide layer when Love waves are produced, in addition to insulating the IDT electrode. The insulation layer or the waveguide layer may include at least one of a silicon oxide (SiO$_2$) layer, a silicon nitride (Si$_x$N$_y$) layer, a zinc oxide (ZnO) layer, a parylene layer, a polymethyl methacrylate (PMMA) layer, or the like, or a combination thereof. Other electrically insulating polymers listed above, may also be used as the insulation layer. For example, only the silicon oxide layer may be used, or both the zinc oxide layer and the silicon oxide layer may be used in such a manner that the zinc oxide layer is coated with the silicon oxide layer.

The fingers of the IDT electrode may include a bidirectional type, a single-phase unidirectional transducer (SPUDT) type, a floating-electrode unidirectional transducer (FEUDT) type, a split type, a reflector type, or the like, and at least one type of the fingers may be used.

Figure 2:
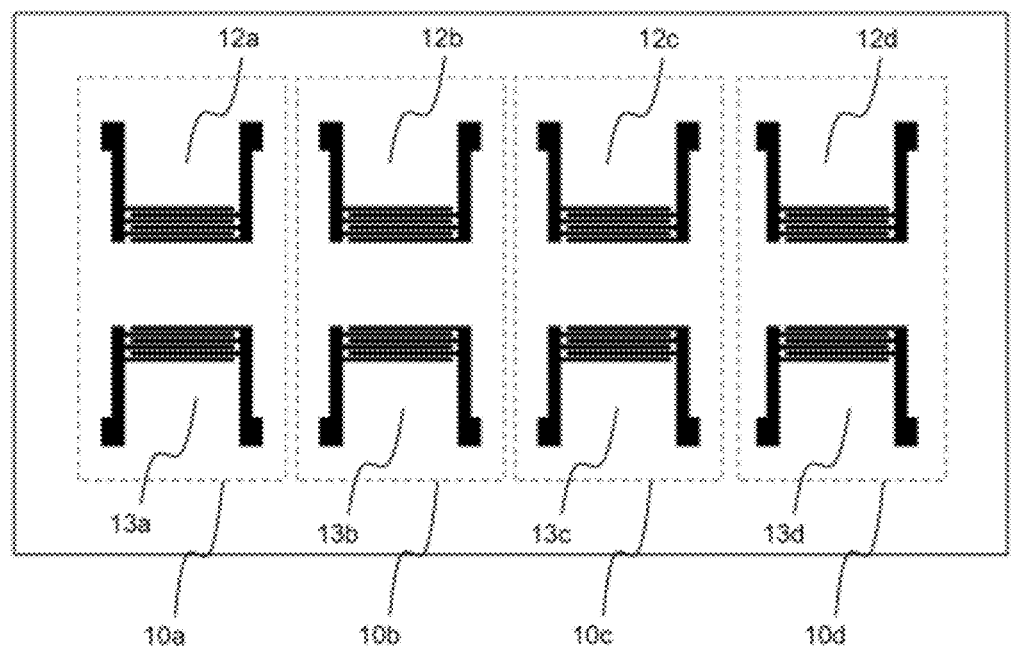
FIG. 2 schematically illustrates an exemplary embodiment of a conventional SAW sensor.

FIG. 2 schematically illustrates an exemplary embodiment of a conventional SAW device. Referring to FIG. 2, the SAW device include unit structures 10a, 10b, 10c and 10d in which input IDTs 12a, 12b, 12c and 12d are disposed so as to correspond to output IDTs 13a, 13b, 13c and 13d respectively, i.e. a single-input single-output (SISO) structure. Thus, the input IDTs 12a, 12b, 12c and 12d correspond to the number of arranged input-output IDT unit structures. This conventional device produces a significant amount of noise and cross-talk because of the numerous input IDTs 12a, 12b, 12c and 12d and the numerous output IDTs 13a, 13b, 13c and 13d all of which are clustered together in close proximity to each other.

Referring to FIG. 1 again, the SAW device includes the single input IDT 121 and the multiple output IDTs 131a, 132a, 133a and 134a, which are arranged in a single-input multi-output (SIMO) structure. That is, a plurality of the output IDTs 131a, 132a, 133a and 134a are arranged to be parallel to the longitudinal direction of the single input IDT 121. In one embodiment, the interdigitated fingers of the output IDTs are parallel to the interdigitated fingers of the input IDTs.

Thus, the SAW device may be used as a sensor in that it has an arrangement structure for sensing two or more target materials. The arrangement shown in the FIG. 1 is capable of fundamentally interrupting the noise and interference that may be generated from the structure shown in the conventional SAW device of the FIG. 2. This is because only as many IDT sites are utilized on the single IDT 121 as the number of desired detection targets. In addition, the sensor itself is downsized (i.e., reduced in size), so that the SAW device advantageously increases yield, and reduces the quantity of samples used for sensing.

According to an exemplary embodiment, the four output IDTs 131a, 132a, 133a and 134a are arranged in a row in the longitudinal direction of the single input IDT 121. The number of output IDTs may be two or more within the limited length of the finger of the input IDT 121.

The length $W_{in}$ of the finger of the input IDT is longer than the length $W_{out}$ of the finger of the output IDT. If the length $W_{in}$ of the finger of the input IDT increases, the number of output IDTs may increase, and simultaneously the insertion loss ("IL") of the input IDT may increase according to the equations (1) and (2) below (where, $W=W_{in}$). As a result, if the length $W_{in}$ of the finger of the input IDT is increased excessively, the device may cease to function as a sensor.

Thus, a maximum value of the length $W_{in}$ of the finger (e.g., a single finger) of the input IDT is determined by the IL of the input IDT. The IL of the input IDT can be represented by the following Formula (1) and (2):

$$IL = -20 \log |Y| \quad (1)$$

$$Y = Y_0(W/\lambda) \quad (2)$$

where Y is the total input admittance, $Y_0$ is a characteristics admittance, $\lambda$ is a wave length and W is a finger length.

The IL value can be various numbers and determined based on a final application of the device. Typically, when the IL of the input IDT 121 is −30 dB, the length $W_{in}$ of the finger of the input IDT is regarded as the maximum length (represented by the multiple of a wavelength).

Figure 3:
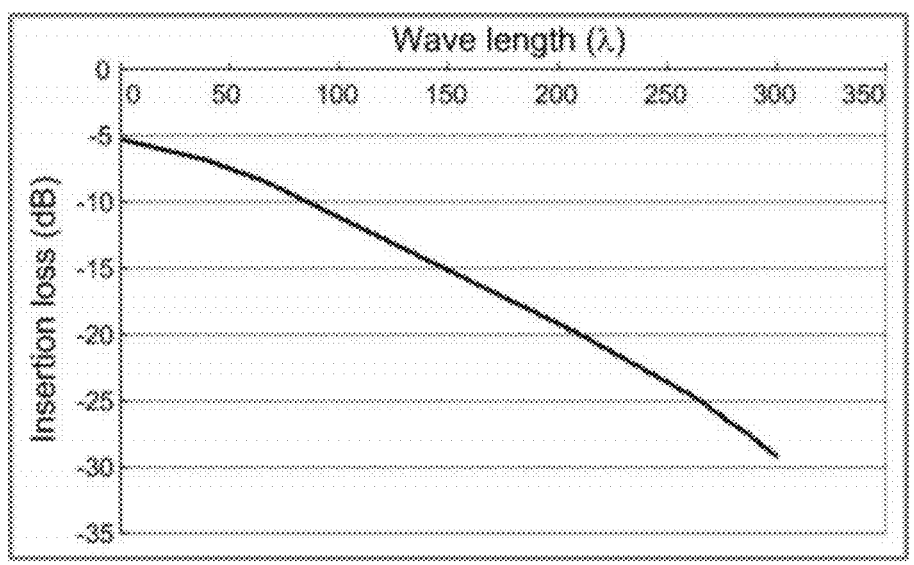
FIG. 3 is a graph that shows a result of simulating the insertion loss of an input IDT.

FIG. 3 is a graph that shows a result of simulating the IL of an input IDT, when the input and output IDTs are disposed such that one wavelength (1λ) is 20 micrometers ("μm").

Referring to FIG. 3, as the length $W_{in}$ of the finger of the input IDT decreases, the IL decreases. However, since the length $W_{in}$ of the finger of the input IDT in the sensor is proportional to an area of the sensing layer corresponding to the delay lines, if the length $W_{in}$ of the finger of the input IDT decreases, the sensed area also decreases. The maximum value of the length $W_{in}$ of the fingers of the input IDT depends on the allowable IL. When −30 dB is generally regarded as a maximum loss of the sensor, the maximum value of the length $W_{in}$ may be about 300λ, where λ is the wavelength of the surface acoustic wave. Meanwhile, when the length $W_{out}$ of the finger of the output IDT is at least 40λ to 50λ, a minimum value of the length $W_{in}$ of the finger of the input IDT is about 80λ to 100λ because at least two output IDTs are arranged in a transverse direction.

The length $W_{in}$ of the finger of the input IDT, the length $W_{out}$ of the finger of the output IDT, and the number m of output IDTs can be represented by Formula (3) below.

$$m = \frac{2W_{in}}{W_{out}} \quad (3)$$

Figure 4:
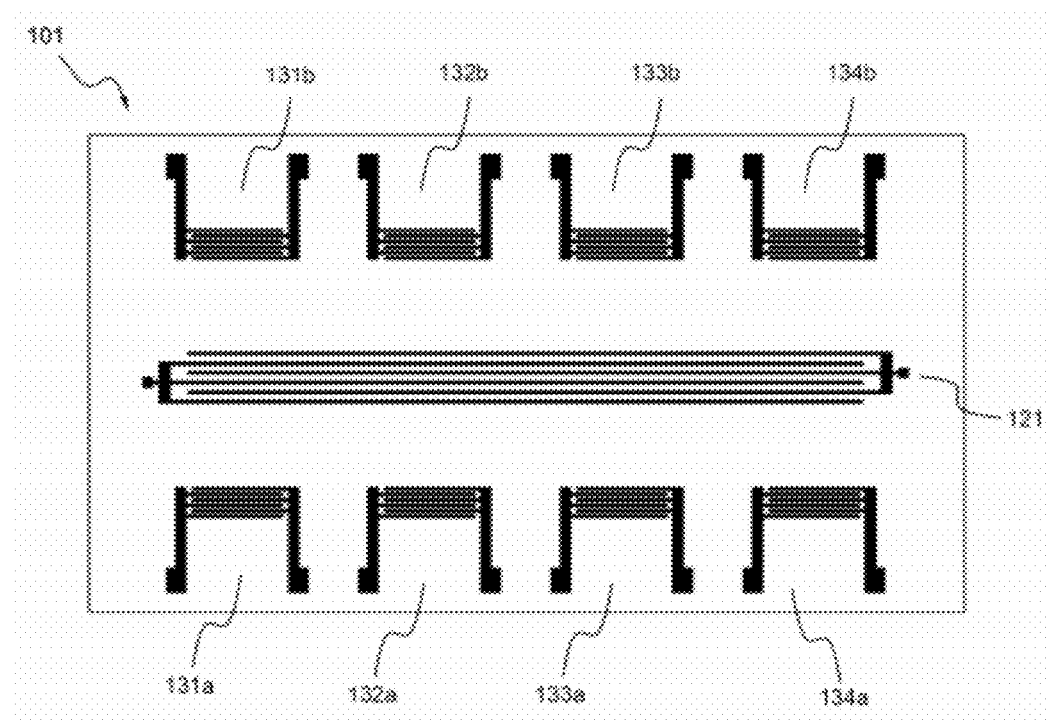
FIG. 4 schematically illustrates another exemplary embodiment of a SAW device.

This is because the output IDTs 131a, 132a, 133a and 134a; and 131b, 132b, 133b and 134b may be disposed on upper and lower sides of the single input IDT 121, respectively (see FIG. 4).

The output IDTs have the maximum number $m_{max}$ when the length $W_{in}$ of the finger of the input IDT is the maximum value and when the length $W_{out}$ of the finger of the output IDT is the minimum value. For example, as in Formula 4 below, when $W_{in}$ is the maximum value of 300λ, and when $W_{out}$ is the minimum value of 50λ, $m_{max}$ is 12, which means that there can be 12 output IDTs per input IDT.

$$m_{max} = (2 \times 300\lambda)/50\lambda = 12 \quad (4)$$

In an exemplary embodiment, the minimum length $W_{out}$ of the finger of the output IDT is set to 50λ. However, the minimum length $W_{out}$ may be properly set according to the device, and is therefore not limited.

In one embodiment, two or more of the output IDTs 131a, 132a, 133a and 134a may be disposed on a substrate per single input IDT 121. In FIG. 1, the four output IDTs 131a, 132a, 133a and 134a are disposed in a row in the longitudinal direction of the input IDT 121. In another embodiment, two or more output IDTs can be disposed parallel to the input IDT.

Referring to FIG. 4, another exemplary embodiment of the SAW device 101 may include first output IDTs 131a, 132a, 133a and 134a and second output IDTs 131b, 132b, 133b and 134b, which are disposed on an opposite sides of the input IDT 121 from the side on which the first output IDTs 131a, 132a, 133a and 134a are disposed. The sets of first output IDTs and second output IDTs are disposed to lie parallel to each other in the longitudinal direction of the input IDT 121. That is, the first output IDTs 131a, 132a, 133a and 134a and the second output IDTs 131b, 132b, 133b and 134b are disposed so as to correspond to each other in a transverse direction (perpendicular to the longitudinal direction) with the input IDT 121 interposed therebetween. However, the design is not limited to the input IDT 121 being opposite to the output IDTs 131b, 132b, 133b and 134b with delay lines 141b, 142b, 143b and 144b interposed therebetween.

Figure 5:
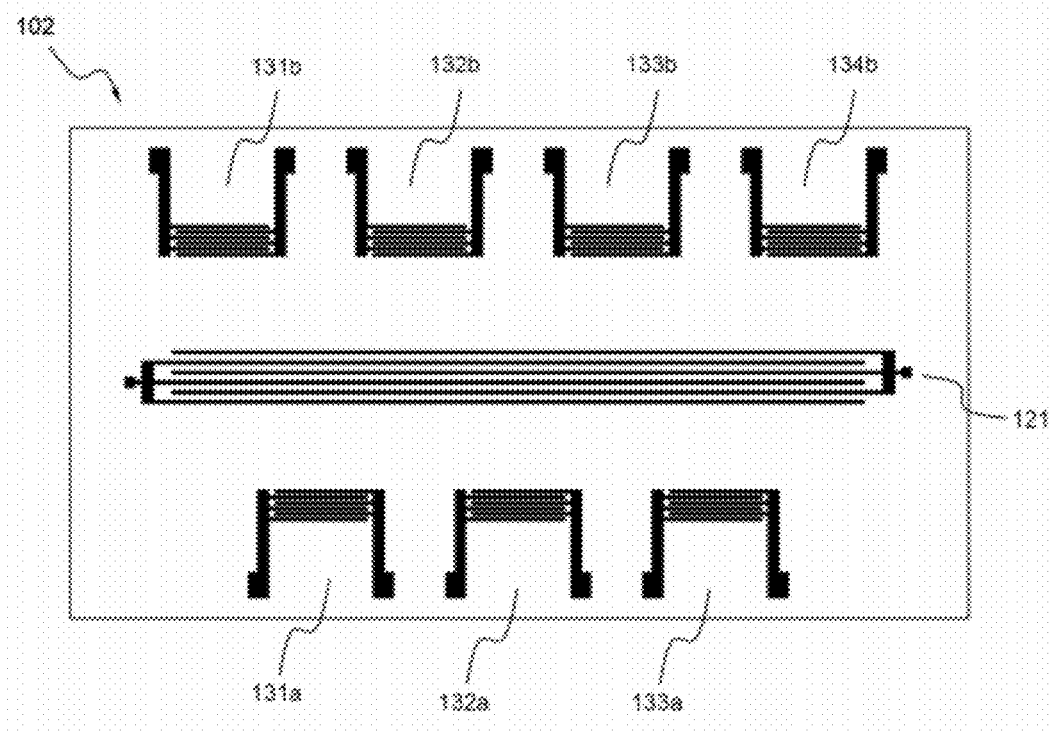
FIG. 5 schematically illustrates an alternative exemplary embodiment of a SAW device.

Referring to FIG. 5, an alternative exemplary embodiment of the SAW device 102 may include first output IDTs 131a, 132a and 133a and second output IDTs 131b, 132b, 133b and 134b, which are disposed in a zigzag form with the input IDT 121 interposed therebetween.

Operation of SAW Sensor

Figure 15:
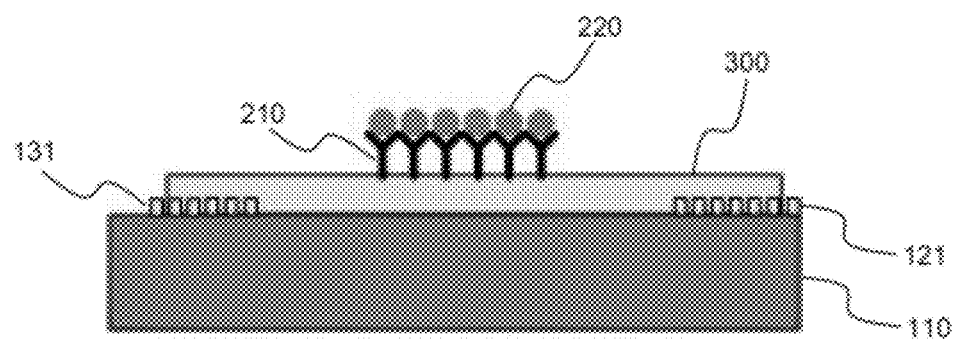
FIG. 15 is a cross-sectional view of a SAW biosensor according to Third Experimental Example.

The exemplary embodiments of the SAW devices 100, 101 and 102 may include a sensor for sensing a target material. A driving principle of the SAW sensor 100 will be described with reference to FIGS. 1 and 15. An electrical signal generates a mechanical wave while passing through the IDT electrode 121. This wave is changed via physical, chemical and electrical interactions, when the target material 220 in the sample binds to the receptor 210 on the surface of the SAW sensor 100. That is, a central frequency, phase, or signal intensity of the output signal of the SAW sensor is changed when the target material binds to (reacts with) the receptor 210 on the surface of the SAW sensor 100. For example, when the weight of the receptor is changed by the binding of the target material 220, the shear velocity of the SAW excited by the input IDT 121 is changed, and the oscillation frequency of the output IDT 131 receiving the SAW of the changed shear velocity is changed. Accordingly, physical properties of the target materials 220 may be precisely detected by measuring the change of the oscillation frequency. In addition, the target material 220 may be qualitatively and quantitatively analyzed.

The SAW generically refers to waves, which concentrate and transmit energy on the vicinity of the surface of a medium. The SAW can be excited and received by the IDT electrodes 121 and 131 disposed on the surface of the piezoelectric substrate 110. The SAWs used for the SAW device may include a shear horizontal (SH) wave, a Love wave, a leaky surface acoustic wave, and the like, in addition to the well known Rayleigh wave.

An exemplary embodiment of the SAW device may use the Love wave. A mode of the Love wave generally has an effective coupling coefficient and a low loss, compared to that of the leaky wave, such as the Rayleigh wave or the SH wave. When the Love wave is used, a surface layer 300 (see FIG. 15) may include a high-density dielectric layer or polymer layer, in which the speed of sound is slow so as to form a waveguide path on the piezoelectric substrate 110. The Love wave reduces the speed of a surface wave, and makes the speed of the surface wave slower than that of a slow transverse wave. Therefore, the Love wave is known as the surface wave, which concentrates the energy of a bulk wave having only a transverse wave on the vicinity of the surface of the substrate 110.

In one embodiment, the SAW device may be constructed so as to make multiple measurements rapidly for purposes of affecting a combinatorial method of measuring sample properties. An exemplary device of this nature is depicted in the FIGS. 18 to 20 which will be discussed in detail below.

The high-density dielectric layer may include a metal oxide layer or a polymeric layer. The high-density dielectric layer may include, but is not limited to, tantalum pentoxide ($Ta_2O_5$), zinc oxide (ZnO), sapphire ($Al_2O_3$), titanium dioxide (rutile) ($TiO_2$), niobium pentoxide ($Nb_2O_5$), bismuth germanium oxide ($Bi_{12}GeO_{20}$; BGO), bismuth trioxide ($Bi_2O_3$), or the like, or a combination comprising at least one of the foregoing metal oxides. The polymer layer may include, but is not limited to, parylene, polymethyl methacrylate (PMMA), benzocyclobutene (BCB), polyolefins, polycarbonates, polystyrenes, polyesters, polyamides, polyamideimides, polyarylates, polyarylsulfones, polyethersulfones, polyphenylene sulfides, polysulfones, polyimides, polyetherimides, or the like, or a combination comprising at least one of the foregoing polymers.

In another exemplary embodiment, the SAW sensor may be applied to an oscillation method, and may further include an external resonator (not shown). The resonator is a circuit for generating a sinusoidal signal of a certain frequency, and converts DC energy into AC energy. Frequency signals within a narrow band may be detected by only an output port without an input port.

This SAW sensor may analyze physical properties such as mass, pressure, density, viscosity, or the like, of the target material. Further, the SAW sensor described herein may obtain a greater change in frequency than a comparative sensor, and may be used to determine characteristics of a sample in a liquid phase or in a gas phase. The SAW sensor has at least ten times, or at least fifteen times, or at least twenty times, a greater excited frequency, compared with that of an existing comparative biosensor.

In one embodiment, the SAW sensor may be fabricated in a small size due to ease of integration and manufacturing, be measured in real time, and reduce the sample size that needs to be used for a measurement. Accordingly, the SAW sensor may used as a biosensor for detecting physical properties or characteristics of the target material to be biologically detected. The biosensor may be used to detect characteristics and properties of biological materials such as enzymes, fungi, proteins, nucleic acids and other biological tissues. In another embodiment, as will be detailed below, the device may include a plurality of SAW devices to conduct rapid testing on a large number of samples.

Figure 18:
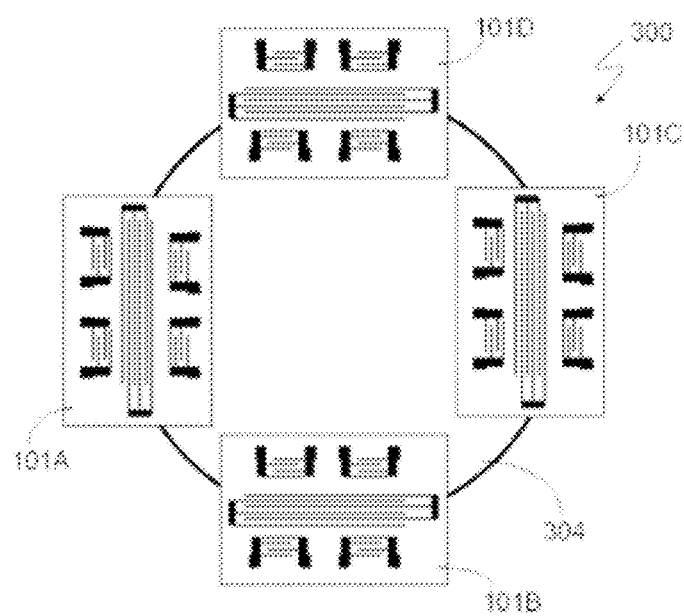
FIG. 18 is a top view of a schematic diagram of an exemplary device that comprises a plurality of SAW devices.
Figure 19:
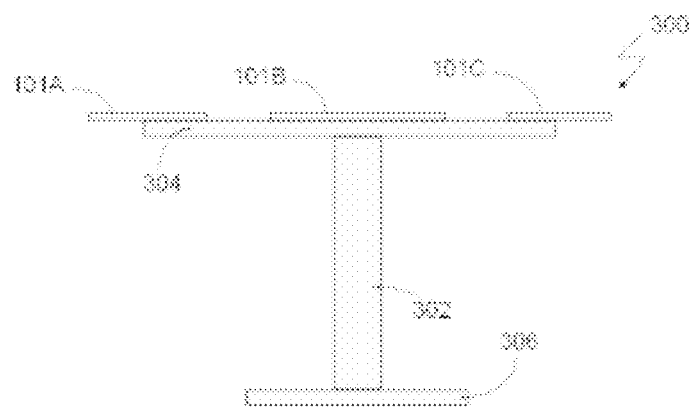
FIG. 19 is a side view of the device of the FIG. 18.

In one embodiment, in one method of proceeding to measure large amounts of different kinds of samples, such as is conducted in newer techniques such as combinatorial chemistry, a plurality of SAW devices 101 (as seen in the FIG. 4) may be disposed upon a rotary table or platform. The FIGS. 18 and 19 depict the top view and side view respectively of one such device 300. In the device 300, a plurality of SAW devices 101A, 101B, 101C and 101D are disposed upon a rotary platform 304. While the FIG. 18 shows only four SAW devices 101A, 101B, 101C and 101D disposed upon the rotary platform 304, fewer or larger numbers of the SAW devices may be disposed upon the rotary platform 304. The rotary platform 304 rotates about a vertical axis disposed in the vertical support 302. The vertical support 302 is disposed upon a base plate 306 as shown in FIG. 19.

Figure 20:
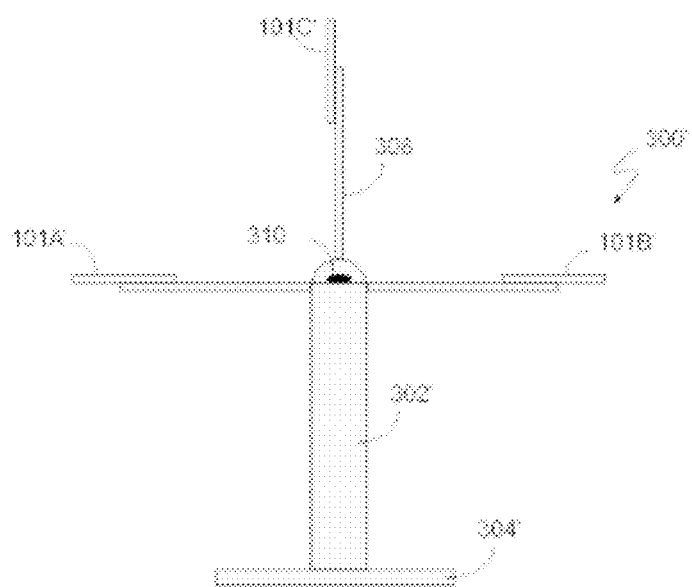
FIG. 20 is a side view of a schematic diagram of another exemplary device that comprises a plurality of SAW devices.

The FIG. 20 depicts another embodiment, of such a device 300'. In the FIG. 20, the individual SAW devices 101A', 101B', 101C' and 101D' are disposed upon rotary arms 308 that rotate about a horizontally disposed shaft 310. The horizontal shaft 310 is supported on a vertical support 302' (or a pair of vertical supports if desired) that is disposed upon a base plate 306'. The devices depicted in the FIGS. 18, 19 and 20, can be used for rapid testing of a large number of samples. They can be advantageously used for combinatorial testing of samples.

In the FIGS. 18-20 above, the rotary platform 304 and the rotary arms 308 may be manufactured from a dielectric material. Examples of dielectric materials are provided above.

In one embodiment, a method of manufacturing a surface acoustic wave device comprises disposing a single input inter-digital transducer on a piezoelectric substrate, the input inter-digital transducer converting a first electrical signal into a surface acoustic wave signal; disposing a plurality of output inter-digital transducers on the piezoelectric substrate, the output inter-digital transducers converting the surface acoustic wave signal into a second electrical signal; and disposing a delay line between the input inter-digital transducer and the output inter-digital transducers, wherein the plurality of the output inter-digital transducers are arranged in a longitudinal direction of the input inter-digital transducer.

In another embodiment, a method of manufacturing the surface acoustic wave device comprises disposing upon a substrate a transmitter where the transmitter is operative to generate a surface acoustic wave. At least two receivers are disposed on the substrate, the receivers converting the received surface acoustic wave into an electrical signal to receive the surface acoustic wave. A receptor that reacts/interacts with the target material is immobilized between the transmitter and the receivers. The generated surface acoustic wave is dependent upon the receptor-target material combination. Thus the target material is detected.

In yet another embodiment, the method may further comprise disposing a plurality of surface wave acoustic devices on a surface that rotates; the surface rotating about a vertical axis or a horizontal axis.

The target material 220 may include biomolecules such as proteins, antibodies, antigens, DNA, RNA, bacteria, animal cells, viruses, tissues or the like, or biological solutions such as toxins produced thereby.

If the target material 220 is the biological solution, the receptor 210 which specifically binds to the target material 220 may include proteins, antibodies, antigens, enzymes, DNA, RNA, peptide nucleic acid (PNA) (artificial DNA), cells, olfactory nerves, or the like.

For example, a disease may be checked by using the SAW biosensor in which the receptors 210 are those that specifically react to a certain bacteria that cause the disease. At this time, the SAW sensor may be used to check the disease depending on whether a specimen obtained from a patient reacts with the receptors 210 of the SAW sensor. Further, in an exemplary embodiment, the SAW device may include a plurality of SAW unit sensors, thus a variety of tests may be performed by using a small quantity of sample in a quick and efficient manner.

Hereinafter, the exemplary embodiments and experimental examples of the invention will be described in further detail. However, it is not intended to limit the scope of the invention.

EXAMPLE

Figure 6:
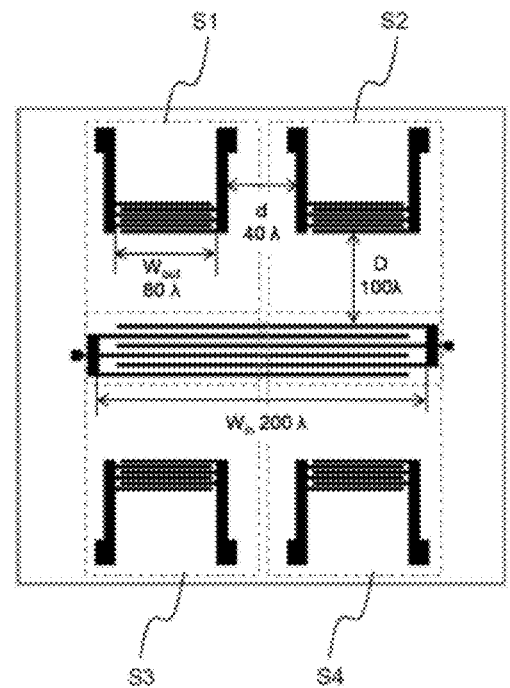
FIG. 6 schematically illustrates an exemplary embodiment of a SAW sensor including four SAW unit sensors S1, S2, S3 and S4.

As schematically illustrated in FIG. 6, the size of a substrate is 8 mm×10 mm, the length $W_{in}$ of the finger of the input IDT is 200λ (where 1λ is 20 μm), and the number of fingers for the input IDT is 50 (in FIG. 6, only six fingers are symbolically shown in each IDT). The length $W_{out}$ of the finger of the output IDT is 80λ, and the number of fingers of each output IDT is 50. The IDTs are formed by the deposition of aluminum (Al), wherein two output IDTs are disposed on each side of the input IDT, and thus a total of four output IDTs are disposed for the single input IDT. An interval between the output IDTs is set to 40λ, and the length of the delay line between the input IDT and the output IDT is set to 100λ. Here, one unit sensor includes one output IDT, one input IDT, and one delay line. As a result, the device of the FIG. 6 displays four unit sensors S1, S2, S3 and S4.

For reference, the size of the fabricated sensor is not optimized, but may be reduced if necessary. The reducible portions may include a portion where a pad for an electrode can be connected with an electric circuit at the adjacent output IDTs, the distance between the input IDT and an edge of the sensor, the distance between the output IDT and the sensor edge, the length $W_{out}$ of the finger of the output IDT, and so on.

Experimental Example 1

Figure 7:
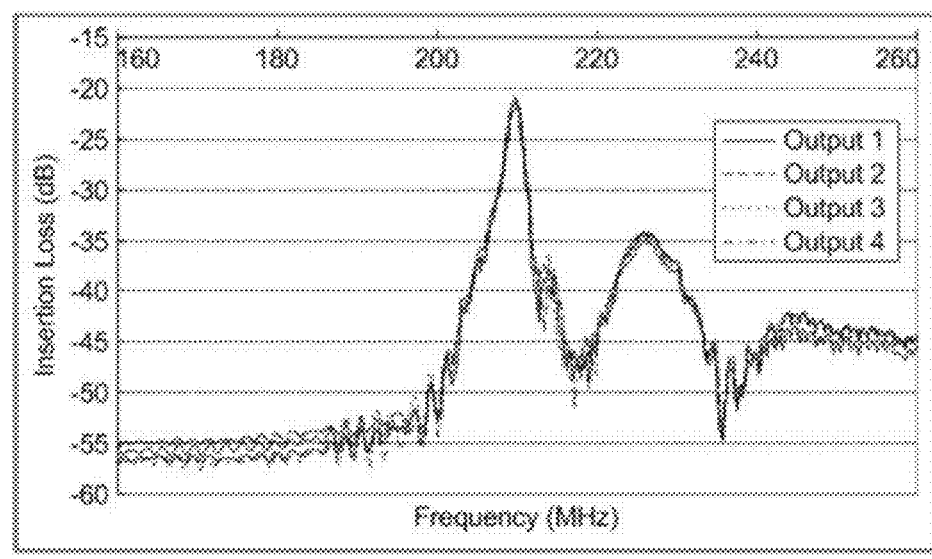
FIG. 7 is a graph that shows all results obtained from measuring frequency characteristics of outputs Output1, Output2, Output3 and Output4 with respect to an input in four SAW unit sensors S1, S2, S3 and S4 according to First Experimental Example.
Figure 8:
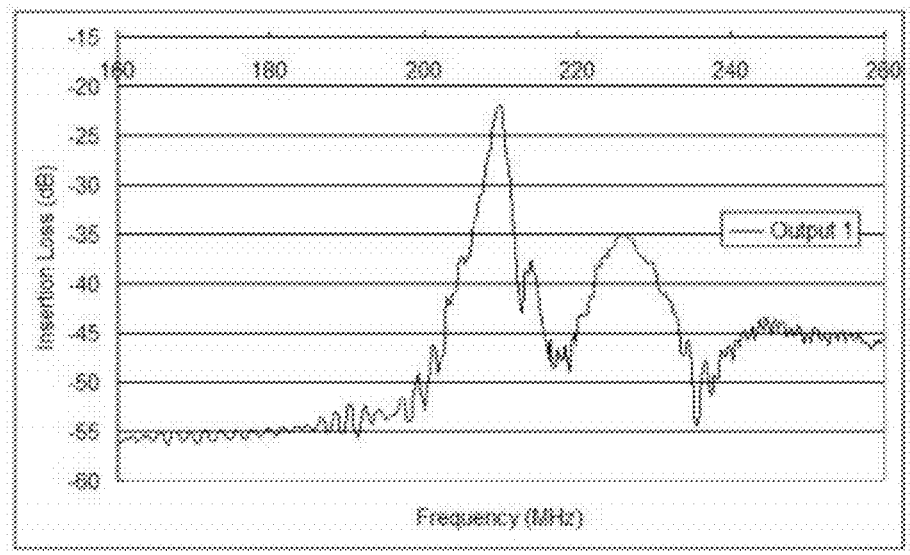
FIG. 8 is a graph that shows results of measuring frequency of Output1 of the sensor S1, with respect to an input in the First Experimental Example.
Figure 9:
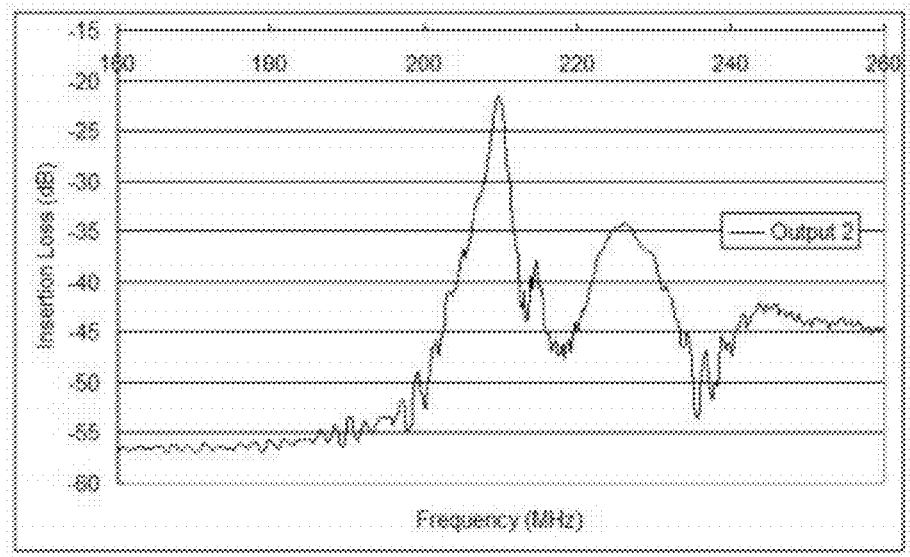
FIG. 9 is a graph that shows results of measuring frequency of Output2 of the sensor S2, with respect to an input in the First Experimental Example.
Figure 10:
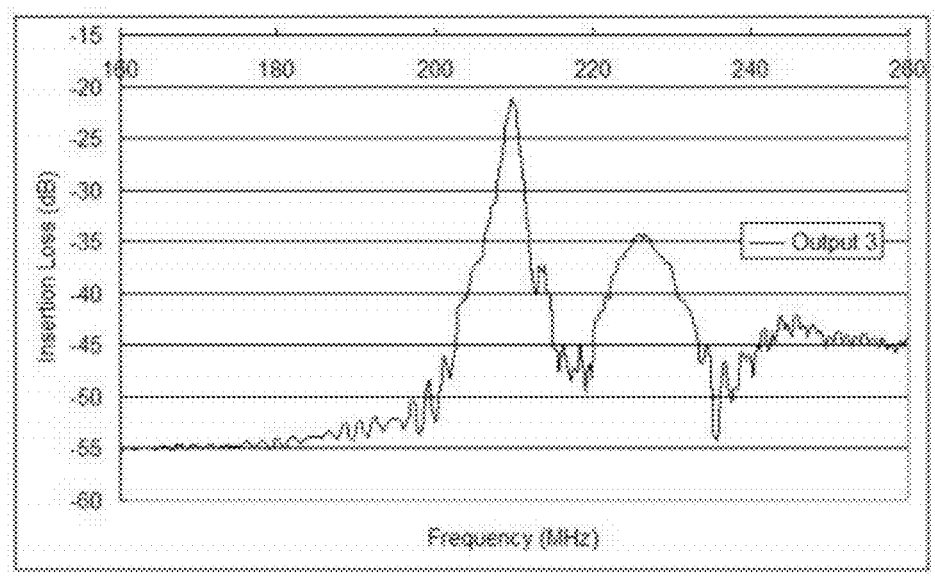
FIG. 10 is a graph that shows a result of measuring frequency of Output3 of the sensor S3, with respect to an input in the First Experimental Example.
Figure 11:
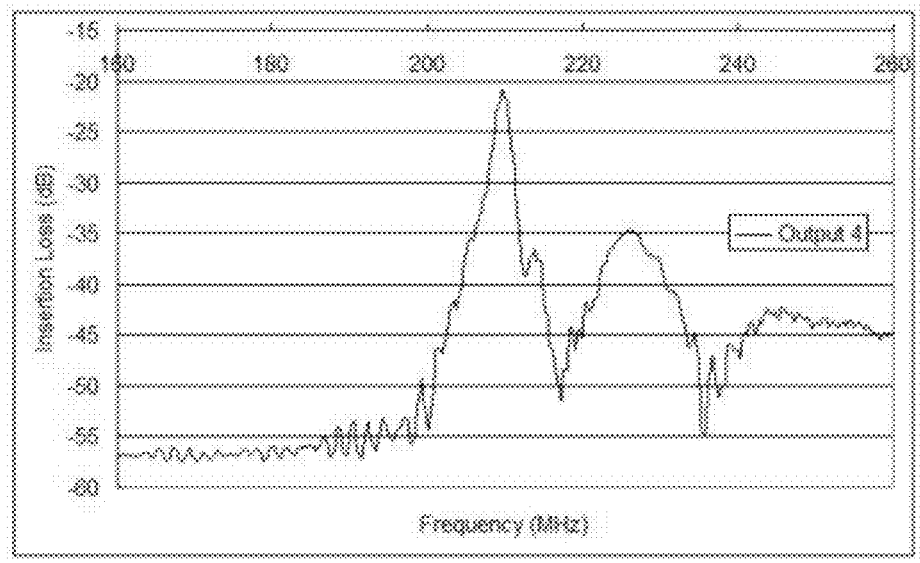
FIG. 11 is a graph that shows a result of measuring frequency of Output4 of the sensor S4, with respect to an input in the First Experimental Example.

Measurement of Frequency Characteristic of Output with Respect to Input Frequencies measured from the four output IDTs of the four unit sensors S1, S2, S3 and S4 are shown in FIGS. 7 to 11, respectively. FIG. 7 shows all of the outputs from the four unit sensors S1, S2, S3 and S4 on a single plot, while the FIGS. 8 through 11 show the outputs of the individual sensors S1, S2, S3 and S4 respectively. As may be in these figures, it is found that the four output signals are substantially similar to each other.

Experimental Example 2

Measurement of Interference Between Output IDTs

The interference between the output IDTs is checked by measuring the level of power between the output IDTs with a network analyzer (available from Agilent, 8753ES).

Figure 12:
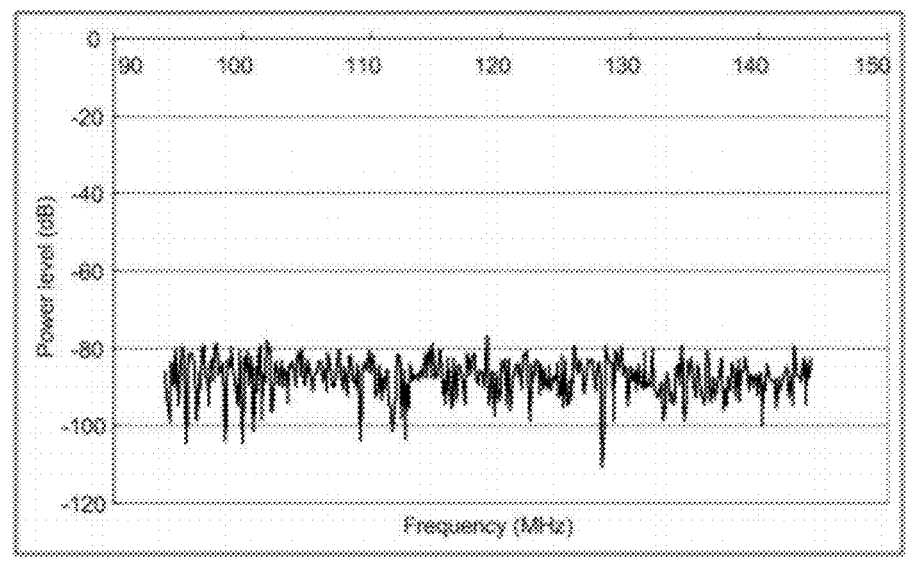
FIG. 12 is a graph that shows a result of measuring interference between output IDTs of diagonal unit sensors S2 and S3 in Second Experimental Example.

First, the interference between the diagonal output IDTs S2 and S3 is measured, and its result is shown in FIG. 12.

It may be found from FIG. 12 that the power level is less than −80 dB, and there is no measurement error caused as a result of interference between the diagonal output IDTs S2 and S3.

Figure 13:
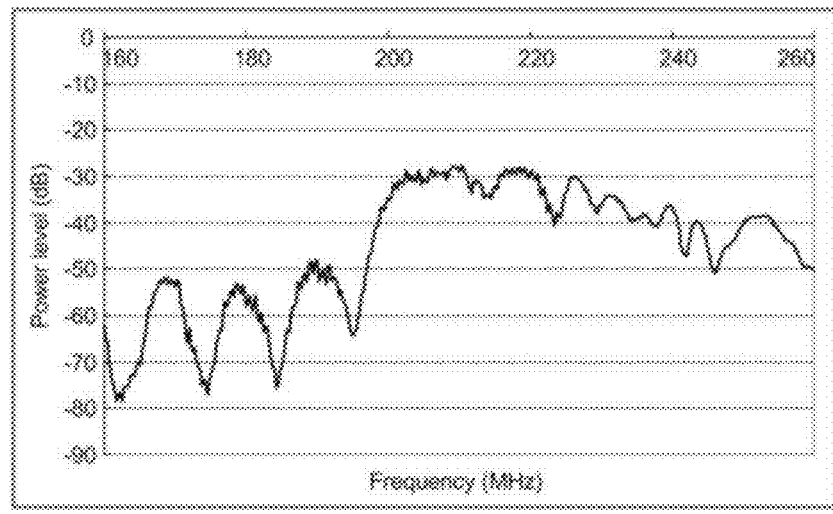
FIG. 13 is a graph that shows a result of measuring interference between output IDTs of opposite unit sensors S2 and S4 in the Second Experimental Example.

The interference between the output IDTs S2 and S4 opposite each other from input IDT was measured, and the result is shown in FIG. 13.

It may be found from the FIG. 13 that the maximum power level is less than −30 dB, which is higher than that between the diagonal output IDTs, and as a result, no interference exists between S2 and S4 because no peak point is generated from a signal form, compared with normal input and output characteristics.

Figure 14:
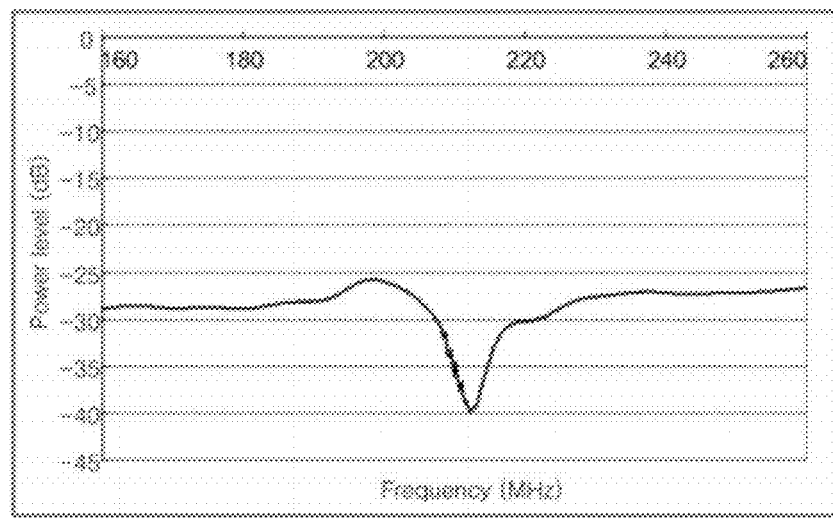
FIG. 14 is a graph that shows a result of measuring interference between output IDTs of adjacent unit sensors S3 and S4 in the Second Experimental Example.

The interference between the adjacent output IDTs S3 and S4 is measured, and its result is shown in FIG. 14.

It may be found from FIG. 14 that no interference exists because the signal form indicates that it could not have influence on a normal signal.

Experimental Example 3

Measurement of Target Proteins IgG

Figure 16:
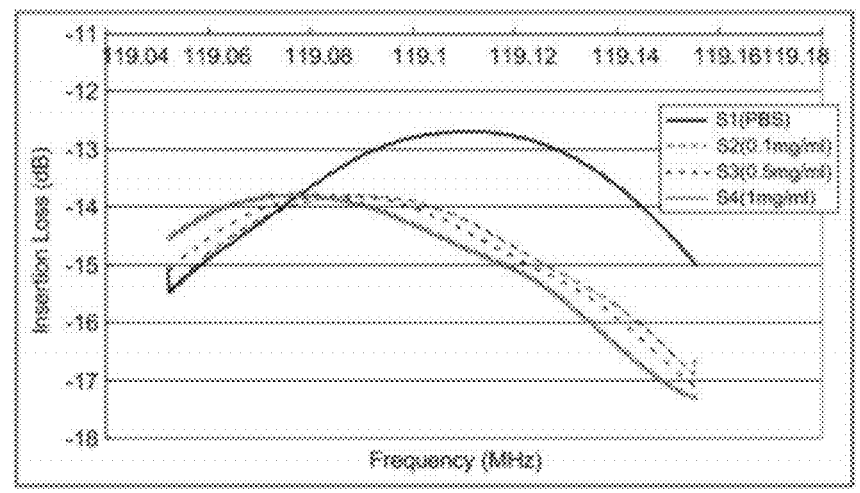
FIG. 16 is a graph that that depicts a result of measuring frequency characteristics between an input and an output on the basis of a reaction between a receptor and a target material in four unit sensors S1, S2, S3 and S4 in Third Experimental Example.

First, protein A, a receptor is immobilized to the surface of the sensor at different concentrations, and then a first central frequency is measured from the input and output IDTs. The target proteins IgG to be sensed are reacted with the receptor, and then a second central frequency is measured. A difference between the measured first and second central frequencies is checked, and the result is shown in FIG. 16. From the total of four output IDTs, S1 is used as a reference sensor. A phosphate buffered saline (PBS) buffer is mixed with the receptor for the reference sensor, while samples containing different proteins IgG are mixed with the receptor and then the target proteins may react with the receptor for the other three sensors S2, S3 and S4. A change in frequency is witnessed at each concentration, because of the increase in mass at each of the other three sensors S2, S3 and S4.

Figure 17:
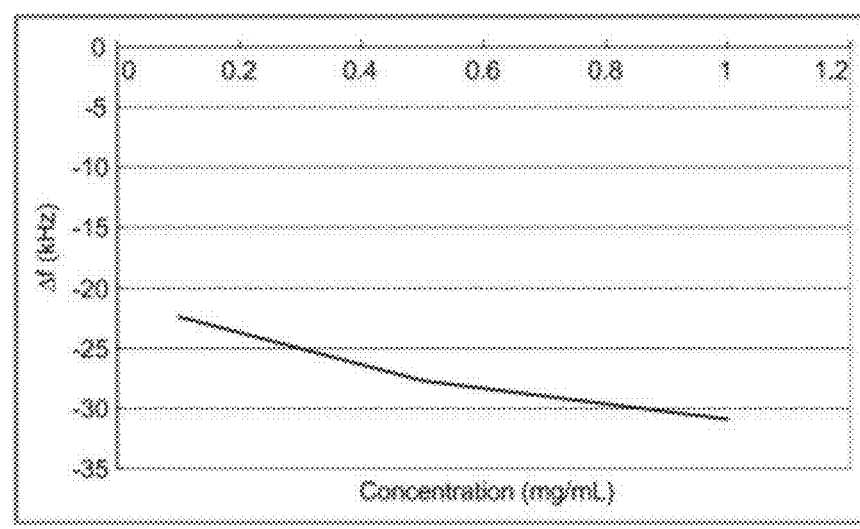
FIG. 17 is a graph showing an amount of reduction in frequency according to concentration on the basis of a reference sensor. This result was obtained from the Third Experimental Example.

As a result of the experiment above, S1 is the reference sensor, and the reaction is performed when the concentrations of the proteins IgG to be sensed for S2 to S4 are 0.1 mg/mL, 0.5 mg/mL, and 1 mg/mL respectively. It is found from this result that as the concentration increases, i.e., the mass increases, the reduction in the frequency increases. The amount of the reduction in the frequency at each concentration on the basis of the reference sensor is shown in Table 1 below as well as in the FIG. 17.

TABLE 1

| Concentration of IgG (mg/mL) | Δf (kHz) |
| --- | --- |
| 0.1 | −22.4 |
| 0.5 | −22.7 |
| 1.0 | −30.9 |

While exemplary embodiments have been disclosed herein, it should be understood that other variations may be possible. Such variations are not to be regarded as a departure from the spirit and scope of exemplary embodiments of the present application, and all such modifications are intended to be included within the scope of the following claims.

What is claimed is:

1. A surface acoustic wave device comprising:
a piezoelectric substrate;
a single input inter-digital transducer disposed on the piezoelectric substrate, the input inter-digital transducer converting a first electrical signal into a surface acoustic wave signal;
a plurality of output inter-digital transducers disposed on the piezoelectric substrate, the output inter-digital transducers converting the surface acoustic wave signal into a second electrical signal; and
a delay line between the input inter-digital transducer and the output inter-digital transducers,
wherein at least two of the output inter-digital transducers are arranged in a row parallel to a longitudinal direction of the input inter-digital transducer, and the input inter-digital transducer includes fingers; each finger having a length such that an insertion loss of the input inter-digital transducer represented by Formula (1) and (2) below is less than −30 dB:

$$IL = -20 \log |Y| \quad (1)$$

$$Y = Y_0(W/\lambda) \quad (2)$$

where IL is insertion loss, Y is total input admittance, and $Y_0$ is characteristic admittance, $\lambda$ is a wave length and W is a finger length.

2. The surface acoustic wave device of claim 1, wherein each finger of the input inter-digital transducer has a maximum length of 300$\lambda$, where $\lambda$ is the wavelength of the surface acoustic wave.

3. The surface acoustic wave device of claim 1, wherein a length ($W_{in}$) of each finger of the input inter-digital transducer, a length ($W_{out}$) of each finger of each output inter-digital transducer, and number (m) of output inter-digital transducers are represented by Formula (3) below:

$$m = \frac{2W_{in}}{W_{out}}. \quad (3)$$

4. The surface acoustic wave device of claim 3, wherein, when the length of each finger of each output inter-digital transducer is 50$\lambda$, the number of the output inter-digital transducers of the input IDT is in a range from 2 to 12.

5. The surface acoustic wave device of claim 1, wherein the surface acoustic wave signal includes a Love wave.

6. The surface acoustic wave device of claim 5, wherein the piezoelectric substrate includes a dielectric layer or a polymer layer.

7. The surface acoustic wave device of claim 1, wherein the input inter-digital transducer is connected with an external resonator.

8. The surface acoustic wave device of claim 1, further comprising additional output inter-digital transducers, wherein the single input inter-digital transducer located between the output inter-digital transducers and the additional output inter-digital transducers.

9. The surface acoustic wave device of claim 1, wherein the surface acoustic wave device is a SAW sensor, and a receptor that specifically interacts with a target material is immobilized on the delay line.

10. A surface acoustic wave device comprising:
a substrate;
a transmitter disposed on the substrate, the transmitter generating a surface acoustic wave;
at least two rows of at least two receivers, the rows arranged parallel to the longitudinal direction of the transmitter and disposed opposite each other relative to the transmitter on the substrate, the receivers receiving the surface acoustic wave (SAW) and converting the received SAW into an electrical signal; and
a receptor immobilized between the transmitter and the receivers, the receptor interacting with a target material;
wherein the transmitter is an inter-digital transducer (IDT) that includes fingers, each finger having a length such that an insertion loss of the input inter-digital transducer represented by Formula (1) and (2) below is less than −30 dB:

$$IL = -20 \log |Y| \quad (1)$$

$$Y = Y_0(W/\lambda) \quad (2)$$

where IL is insertion loss, Y is total input admittance, and $Y_0$ is characteristic admittance, $\lambda$ is a wave length and W is a finger length.

11. The surface acoustic wave device of claim 10, wherein the transmitter and the receivers are disposed on a surface of the substrate.

12. The surface acoustic wave device of claim 10, wherein the surface acoustic wave is a Love wave.

13. The surface acoustic wave device of claim 10, wherein the at least two rows of receivers are disposed opposite each other centering the transmitter between the at least two rows of receivers.

14. A method of manufacturing a surface acoustic wave device comprising:
disposing a single input inter-digital transducer on a piezoelectric substrate, the input inter-digital transducer converting a first electrical signal into a surface acoustic wave signal;
disposing a plurality of output inter-digital transducers on the piezoelectric substrate, the output inter-digital transducers converting the surface acoustic wave signal into a second electrical signal; and
providing a delay line between the input inter-digital transducer and the output inter-digital transducers, wherein the plurality of the output inter-digital transducers are arranged in a row parallel to a longitudinal direction of the input inter-digital transducer,
wherein the input inter-digital transducer includes fingers; each finger having a length such that an insertion loss of the input inter-digital transducer represented by Formula (1) and (2) below is less than −30 dB:

$$IL = -20 \log |Y| \quad (1)$$

$$Y = Y_0(W/\lambda) \quad (2)$$

where IL is insertion loss, Y is total input admittance, and $Y_0$ is characteristic admittance, $\lambda$ is a wave length and W is a finger length.

15. The method of claim 14, further comprising disposing a plurality of surface acoustic wave devices on a surface that rotates, the surface rotating about a vertical axis or a horizontal axis.

16. A method of using a surface acoustic wave device comprising:
reacting a target material with a receptor of a surface acoustic wave device of claim 9.

17. A device comprising a plurality of surface acoustic wave devices of claim 1 on a rotary platform comprising a vertical support.

* * * * *